United States Patent
Ellenberger-Girard et al.

(10) Patent No.: US 10,105,065 B2
(45) Date of Patent: Oct. 23, 2018

(54) DEVICE FOR APPLICATION OF A SENSOR TO A MEASUREMENT SITE, A SENSOR HEAD, A KIT OF AN APPLICATION DEVICE AND SENSOR AND USE OF AN APPLICATION DEVICE FOR OPTICAL MEASUREMENT OF PHYSIOLOGICAL PARAMETERS

(71) Applicant: SenTec AG, Therwil (CH)

(72) Inventors: Christoph Ellenberger-Girard, Therwil (CH); Dominik Rudmann, Basel (CH); Peter Matthias Schumacher, Kirchlindach (CH)

(73) Assignee: SenTec AG, Therwil (CH)

( * ) Notice: Subject to any disclaimer, the term of this patent is extended or adjusted under 35 U.S.C. 154(b) by 272 days.

(21) Appl. No.: 14/351,276

(22) PCT Filed: Sep. 25, 2012

(86) PCT No.: PCT/EP2012/068851
§ 371 (c)(1),
(2) Date: Apr. 11, 2014

(87) PCT Pub. No.: WO2013/064313
PCT Pub. Date: May 10, 2013

(65) Prior Publication Data
US 2014/0303462 A1 Oct. 9, 2014

(30) Foreign Application Priority Data
Oct. 31, 2011 (EP) .................................. 11187342

(51) Int. Cl.
*A61B 5/1455* (2006.01)
*A61B 5/0205* (2006.01)
(Continued)

(52) U.S. Cl.
CPC ........ *A61B 5/0205* (2013.01); *A61B 5/14546* (2013.01); *A61B 5/14552* (2013.01);
(Continued)

(58) Field of Classification Search
None
See application file for complete search history.

(56) References Cited

U.S. PATENT DOCUMENTS

| 4,003,707 A | 1/1977 | Lübbers et al. |
| 4,005,700 A | 2/1977 | Parker |

(Continued)

FOREIGN PATENT DOCUMENTS

| EP | 0008460 A2 | 3/1980 |
| EP | 1010788 A1 | 10/2000 |

(Continued)

OTHER PUBLICATIONS

Japanese Office Action issued in corresponding Japanese Patent Appln. No. 2014-537540, 5 Pages.

*Primary Examiner* — Eric Winakur
*Assistant Examiner* — Marjan Fardanesh
(74) *Attorney, Agent, or Firm* — Davis & Bujold PLLC; Michael J. Bujold (57) ABSTRACT

A device for applying a sensor to a measurement site on a patient's skin has a wall arrangement defining an applicator volume above the patient's skin. The wall arrangement has a patient's side and a sensor side. At least one gas-permeable membrane separates the applicator volume into a first volume directed to the measuring site at the patient's side of the wall arrangement and a second volume separated from the patient's skin and directed to the sensor side of the wall arrangement.

21 Claims, 4 Drawing Sheets (51) Int. Cl.
*A61B 5/00* (2006.01)
*A61B 5/145* (2006.01)

(52) U.S. Cl.
CPC ........ *A61B 5/14556* (2013.01); *A61B 5/4875* (2013.01); *A61B 5/6833* (2013.01); *A61B 5/6838* (2013.01); *A61B 5/6816* (2013.01); *A61B 2560/0285* (2013.01); *A61B 2560/0443* (2013.01)

(56) References Cited

U.S. PATENT DOCUMENTS

| | | | |
|---|---|---|---|
| 4,274,418 A | * | 6/1981 | Vesterager ......... A61B 5/04082 204/403.06 |
| 4,824,789 A | * | 4/1989 | Yafuso ................ A61B 5/1459 250/227.23 |
| 6,345,191 B1 | | 2/2002 | Hartmann et al. |
| 7,725,149 B2 | | 5/2010 | Peyser et al. |
| 2001/0034479 A1 | | 10/2001 | Ring et al. |
| 2003/0050543 A1 | | 3/2003 | Hartmann et al. |
| 2003/0214655 A1 | | 11/2003 | Weiss et al. |
| 2008/0152180 A1 | * | 6/2008 | Tsai ........................ H04R 7/04 381/338 |
| 2012/0296266 A1 | * | 11/2012 | Malinski ............. A61M 13/003 604/24 |
| 2013/0123589 A1 | * | 5/2013 | Moritani ............ A61B 5/14546 600/309 |

FOREIGN PATENT DOCUMENTS

| | | |
|---|---|---|
| EP | 1040788 A1 | 10/2000 |
| JP | S51110386 A | 9/1976 |
| JP | S5774012 U | 5/1982 |
| JP | S5940844 A | 3/1984 |
| JP | H0933532 A | 2/1997 |
| JP | 2000292354 A | 10/2000 |
| JP | 2009125342 A | 6/2009 |
| WO | 02/056023 | 7/2002 |

* cited by examiner

DEVICE FOR APPLICATION OF A SENSOR TO A MEASUREMENT SITE, A SENSOR HEAD, A KIT OF AN APPLICATION DEVICE AND SENSOR AND USE OF AN APPLICATION DEVICE FOR OPTICAL MEASUREMENT OF PHYSIOLOGICAL PARAMETERS

The invention is directed to a device for application of a sensor to a measurement site, a sensor head, a kit of application device and sensor and use of an application device for optical measurements of physiological parameters on or through the skin according to the independent claims.

Currently, reusable sensor heads for transcutaneous $CO_2$/$O_2$ measurements are affixed to the measuring site by adhesive adaptors after applying a contact fluid on either sensor head or patient's skin. Those adaptors have the only purpose to fix the sensor to the measuring site directly on the patient's skin. After use of such adaptors a sensor head has to be elaborately cleaned, which leads to high service needs of the sensor, requires training and consequently leads to high costs. Such adaptors are for example known for electrochemical sensors in medical applications from WO 2008/132205.

It is an object of the present invention to avoid the drawbacks of the state of the art and in a particular provide a device for application of a sensor to a measuring site, a sensor head, a kit of application device and sensor and a use of an application device for optical measurements of physiological parameters on or through the skin which facilitates the cleaning and handling of a reusable sensor head. Furthermore the shelf-life and life time of the sensor parts should be as long as possible.

The object is accomplished by a device for application of a sensor to a measurement site according to the independent claims.

The device has at least one application area enabling the application of the device to a patient skin. Furthermore, the device comprises an interface for connecting the device to a sensor head, wherein the device comprises at least a wall arrangement providing an applicator volume above the patient's skin. The wall arrangement comprises a patient's side and a sensor side. At least one gas permeable membrane separates the applicator volume into a first volume being directed to the measuring site at the patient's side of the wall arrangement and a second volume being separated from the patient's skin and directed to the sensor side of the wall arrangement.

A device for application of a sensor to a measurement site comprising at least one gas permeable membrane enables measurements of gases diffusing from the measurement site and still separates the sensor head from a direct contact to the measurement site. This leads to a lower contamination of the sensor head used.

The volume of the first and the second volume each does not exceed 10 $mm^3$ and is preferably smaller than 4 $mm^3$ for sensor application areas of approx. 80 m.

Preferably, the application area comprises an adhesive, which is compatible with the human skin.

The wall arrangement preferably comprises walls that are substantially perpendicular to the measurement site. This way, a volume above the measurement site is created. The wall arrangement can be polyangular, circular or elliptical. The largest extension of the wall arrangement does not exceed 5 cm preferably does not exceed 1.5 cm. Preferably, a sensor head being inserted into the device is still rotatable while being inserted or thereafter. The wall arrangement comprises a patient's side, which is the area of the wall arrangement directly adjacent to the measurement site and a sensor side being the portion of the wall arrangement directed to the sensor. The gas-permeable membrane is arranged substantially in parallel to the measurement site. As a matter of course, the gas permeable membrane can further have other functions or can be combined with additional functional layers. Other functions can for example be electrical insulation and/or partial optical transparency.

Preferably, at least the wall arrangement and the membrane cannot be disassembled without being destroyed.

The interface enables the connection of a sensor head to the device. The interface can comprise a sealing function to prevent significant gas leakage and/or to prevent disturbances of optical measurements by ambient light.

The device does not comprise any electrical or electronical components; as understood herein identification means such as RFID chips, RFID-antennas, or identification resistors and printable electronical or optical components such as, but not limited to, OFETs, OLEDs (organic light emitting diodes), or OPDs (organic photo diodes) are not electronic or electrical components.

The membrane can consist of a polymer, like fluoropolymers, such as PTFE, or Polyester, Polyethylenterephtalat (PET), Polymethylpentene or Parylene or Polyethersulfone (PES), acrylic copolymers, cellophane, rubber or silicon elastomer (silastic) films, or of ceramic or semiconductor or metallic films or thin sheets such as alumina, silica, silicon, silicon nitride, titanium nitride, steels, titanium, aluminium, etc. The membrane can be porous or free of pores or contain deliberately introduced porelike structures, e.g. structured or etched silicon, in particular the membrane can comprise a combination of different porosities such as fine pored and coarse-pored or porous and free of pores.

The gas-permeable membrane can further be fluid-impermeable. The device can also comprise a second fluid-impermeable membrane, additionally to the first, gas-permeable membrane.

A further fluid-impermeable functionality of the membrane or a second fluid impermeable membrane prevents fluids from getting into the second volume. Hence, no fluid originating from the measurement site can get into direct contact with sensor head, which is important in particular for optical measurements.

It is further possible to place a water trap, e.g. a hydrophilic material within the first volume, to intentionally collect the diffusing water from the measurement site.

The gas-permeable membrane can further be electrically insulating. This leads to a suppression of electrostatic discharge events.

The application area and/or the wall arrangement on the patient's site can be provided with a contact medium (e.g. fluid, gel or paste) as common in sensor application on skin Preferably, the contact medium seals the first volume from ambient air and/or from ambient radiation.

Hence, exchange of gas in the first volume with ambient air and/or intrusion of ambient radiation is restricted to an extent such that a significant influence on the measurement result is avoided.

The contact medium and/or the application layer can be covered by a detachable cover layer before use. The contact medium and the adhesive layer on the application area can further be the same layer comprising a medium fulfilling both functions.

A detachable cover layer on the one hand keeps the application layer clean and functional and on the other hand protects the membrane inside the device from external influences during transport or storage.

Such external influences could be mechanical impacts, fluids, gases, or radiation such as ambient light that influence the membrane or other additional layers being arranged within the device, such that the membrane or the additional layers are destroyed or become non-functional.

The second volume or the gas-permeable membrane can comprise one or several gas sensitive dyes, wherein preferably the sensitive dyes are arranged in a layer, which preferably is protected by a protection layer against environmental gases before use. Preferably, the sensitive dyes are sensitive to $CO_2$ (e.g. Calmagite, Naphtol Blue Black, Naphtolphtalein or HPTS (1-hydroxypyren3,6,8-trisulfonate)), $O_2$ (e.g. Ruthenium or Pt and Pd octaethylporphyrins based fluorescent dyes), and/or water vapour (e.g. cobalt(II) chloride, copper(II) chloride, calmagite, etc.). The sensitive dyes can further comprise a pH-indicating dye or a fluorescent dye.

A sensitive layer comprising a sensitive dye can be disposed together with the device. Generally, sensitive dyes only remain stable during a limited time frame. This time frame is significantly shorter than the product life time of a sensor head, especially in case of an optical sensor head. Since the sensitive dye may also be sensitive to atmospheric gases and ambient light, the sensitive layer is preferably protected by a protection layer before use. In addition or alternatively, the sensitive elements of the device may also be protected by gas and light tight packaging of the whole device.

The interface can comprise a sealing element for sealing the second volume from ambient gases and/or ambient radiation in use.

To be able to detect the amount of gas diffusing from the measuring site without significant disturbance from ambient gases a further sealing element suppresses the intrusion of ambient air into the second volume. This leads to more accurate measuring results.

The sealing element can be an elastomer part or some other gastight material.

The gas-permeable membrane can be an at least partly reflecting layer, having reflecting properties at least in a wavelength range from 400 nm to 1 pm, a white layer, or a metallic layer. Alternatively, an additional at least partly reflecting layer, having reflecting properties at least in a wavelength range from 400 nm to 1 pm, a white layer, or a metallic layer can be provided.

If for an intended optical measurement light from the sensor head does not have to penetrate any tissue, by means of a reflecting or white layer or metallic layer, the light emitted from the sensor head can be reflected back to a detector within the sensor head and increase the propagation length within the light-affecting element, which can be a gaseous medium or for example some sensitive dye. Alternatively or additionally, ambient light can be reflected away from the optically sensitive components of device and/or sensor head, which reduces the amount of created but unwanted parasitic signal.

To be able to fix the device to a measurement site the device may be stuck onto the measurement site by means of an adhesive layer. Additionally or alternatively, the device can be clamped onto the measurement site.

The clamping solution is especially advantageous for measuring sites on ears, earlobes, fingers, toes or nose.

The device can comprise means for identification and/or calibration data.

Advantageously, a sensor head can identify what kind of device is being connected to the sensor head. Hence, the handling is simplified and safety is increased. For example the kind of measurement, the sensitive element used, the wavelength required for measurement, and/or the kind of membranes comprised in the device can be coded within the device. Furthermore, if needed even calibration data can be encoded within the device. Preferably, identification and/or calibration data are encoded in a RFID-chip or a resistor arrangement or mechanical identification means.

Preferably, the aforementioned device is for measurement of the concentrations of transcutaneous $CO_2$ and/or transcutaneous $O_2$ and/or water vapour and/or of spectral properties of haemoglobin and/or myoglobin and/or bilirubin and/or water and/or acetone, ethanol or other alcohols, and/or of pulse oximetric $CO_2$ All aforementioned physiological parameters can be determined optically and need a defined measuring site. Some further need a defined measuring volume.

Hence, all parts having a limited shelf life or life time, in particular a shelf life shorter than 1.5 years are disposable. Furthermore, all parts becoming contaminated during use are disposable.

According to another aspect of the invention there is provided a sensor head comprising detection optics for detection of human status variables, preferably for detection of transcutaneous $CO_2$ tension and/or transcutaneous $CO_2$ tension and/or water vapour and/or spectral properties of haemoglobin and/or myoglobin and/or bilirubin and/or water and/or acetone, ethanol or other alcohols, and/or for pulse oximetric measurements of $O_2$. Within the sensor head at least one layer necessary for the sensor's functionality is not provided.

A layer according to the invention comprises complete layers and partial layers.

The layer or layers not being provided can be easily disposed instead of being cleaned and by this facilitates the use of the sensor head.

The layer not being provided, especially in case of an optical, colorimetric or fluorescence measurement sensor head, can be a colorimetric or fluorescent indication layer.

The indication layer can be a colorimetric, such as $CO_2$— or pH sensitive, layer or a fluorescent layer or a combination thereof. Based on a chemical reaction the change of colorimetric or fluorescent indication layer can be detected by the optics and/or electro-optics of the sensor head and the amount of the gaseous medium to be determined can be calculated based on the measuring results.

The sensor head can comprise all necessary optical and electrooptical parts. Alternatively, some of the necessary parts such as the electro-optical parts can be arranged externally. In this case for example the light for the measurement can be conducted to the sensor head by optical fibres.

The layer not being provided, in particular in case of an optical measurement sensor head can be a gas-permeable protection layer, which in addition may also be fluid impermeable.

Since fluid biases measurement results, a fluid-impermeable protection layer leads to more accurate measuring results. The gas permeability is necessary since a gaseous medium has to be able to get into the measuring volume.

The layer not being provided, in particular in case of optical colorimetric, fluorescence and/or absorption measurements, can be a light reflecting layer, having reflecting properties within a wavelength range from 400 nm to 1 pm.

Several layers not being provided can be a combination of single layers not being provided. For example, the layers not being provided, in particular in case of optical colorimetric, fluorescence and/or absorption measurements, can be any combination of a gas-permeable and possibly fluid impermeable protection layer, a fluid impermeable protection layer, an at least partially light reflecting layer, and a colorimetric or fluorescent indication layer.

A light reflecting layer increases the absorption path length in case of absorption measurements. As a matter of course, the reflecting layer does not necessarily have reflecting properties over the complete layer surface. Even a combination of reflecting and non-reflecting areas of the reflecting layer can be useful, for example in case of combined measurements.

Furthermore, there is provided a kit of a sensor head and a device for application of a sensor to a measurement site according to the above mentioned features, where only the combination of the sensor head and the device for application results in a fully functional measurement sensor.

The invention as further explained with reference to preferred embodiments and the following figures which show.

Figure 1:
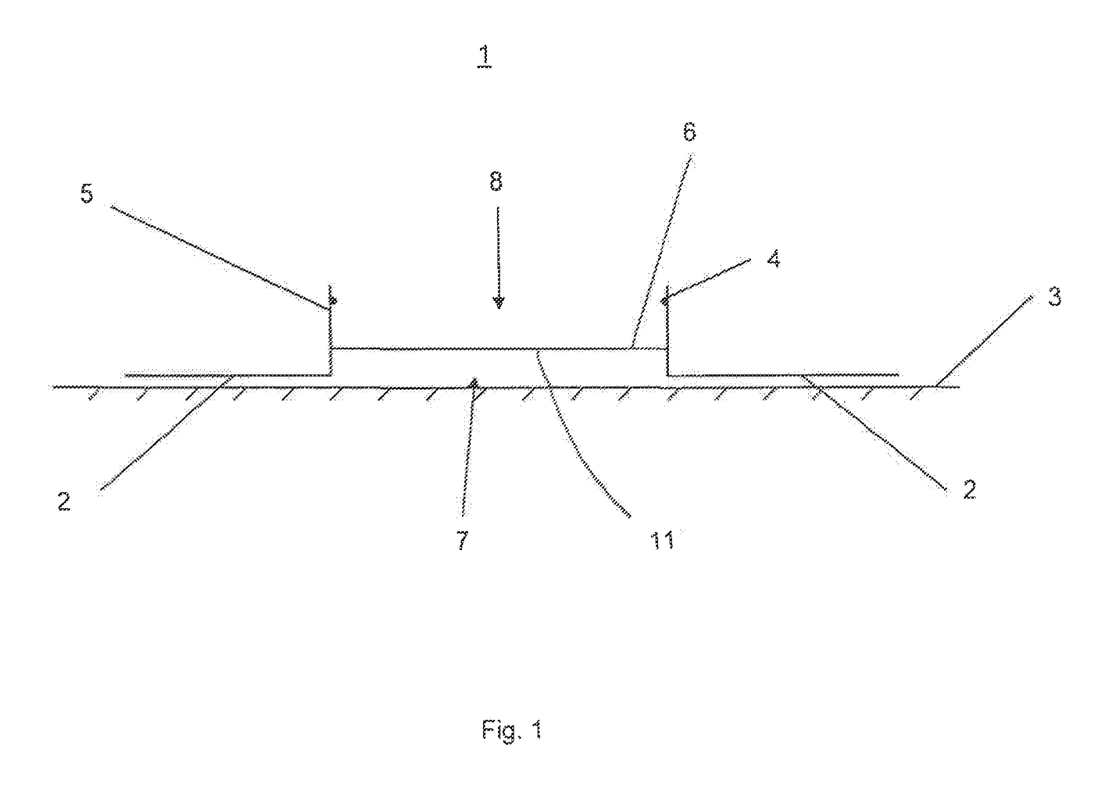
FIG. 1 a schematic view of a device for application of a sensor to a measurement site.

FIG. 1 shows a device 1 for application of a sensor to a measuring site. The device 1 comprises an application area 2 being covered with an adhesive layer. The adhesive layer fixes the device 1 to the skin 3. The device 1 further comprises a wall arrangement 5 which is oriented substantially perpendicular to the application area 2. The wall arrangement 5 can further exhibit different geometrical shapes such as conical elements or grooves. The wall arrangement 5 provides an applicator volume 7 above the skin 3. The wall arrangement can limit the applicator volume in a circular, elliptical or polyangular shape. The wall arrangement 5 is made from plastic material such as ABS or POM or other bio-compatible plastic materials in injection moulding. The wall arrangement could further be stamped or blanked. Furthermore, the wall arrangement 5 comprises an interface 4 which enables the connection with the sensor head. The interface 4 is adapted to fit into a groove being arranged on a sensor head. Preferably, the interface 4 leads to a Poka Yoke connection of the sensor head and the device 1. Hence, the sensor head either fits into the device 1 in a correct manner so that measurements are possible or it does not fit at all. Alternatively or in addition, the sensor head preferably is rotatable in the device 1 during and/or after fitting them together. A gas permeable membrane 6 separates the applicator volume within the wall arrangement 5 into the first volume 7 being directed to the measuring site at a patients' site of the wall arrangement and a second volume 8 being separate from the patients' skin and directed to the sensor site of the wall arrangement 5. Preferably, the membrane 6 further comprises water-impermeable properties. Of course even further layers are possible. The membrane 6 consists of a fluoropolymer such as PTFE. The membrane 6 is covered with a contact medium 11.

Figure 2:
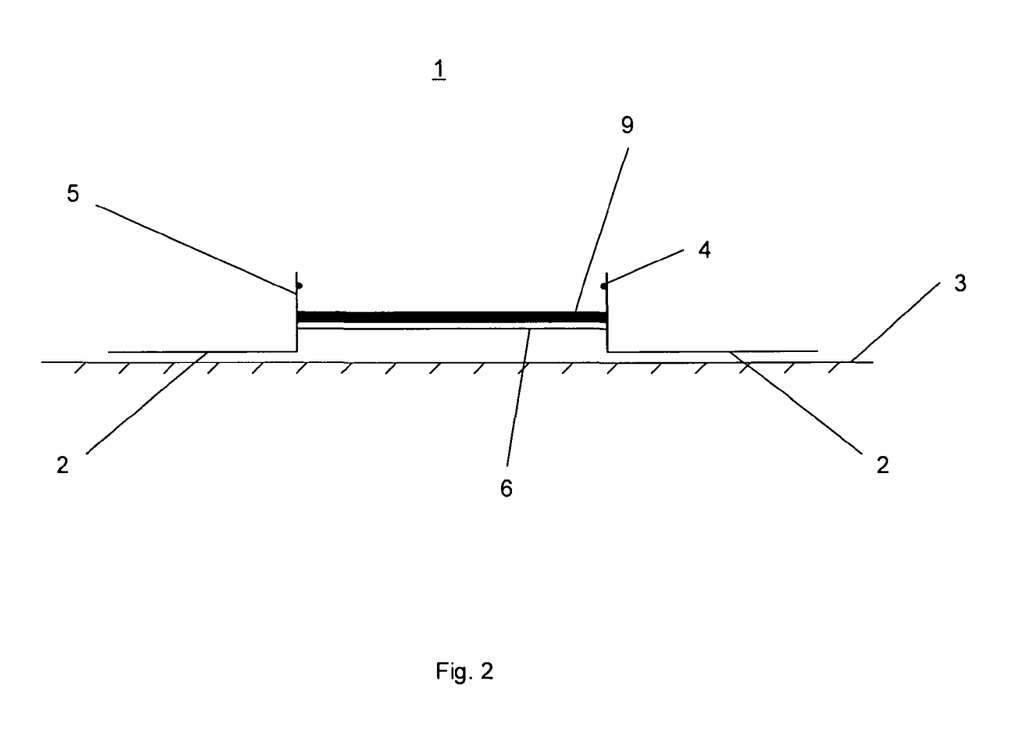
FIG. 2 a schematic view of a device for application of a sensor to a measurement site comprising a membrane with sensitive dye.

FIG. 2 shows a device 1 as described in FIG. 1 comprising an application area 2 being stuck onto the skin 3. The device 1 comprises a wall arrangement 5 and a gas permeable membrane 6. The wall arrangement further comprises an interface 4 adapted to connect the device 1 to the sensor head. Additionally to the gas permeable membrane 6 the device 1 comprises a sensitive layer 9 being able to react to a gaseous medium diffusing from the skin 3. The sensitive layer 9 comprises a pH-indicator which indicates a change in the pH value based on changing partial pressures of $CO_2$ by a colour change. Of course further layers within the wall arrangement 5 are possible. A sensitive layer can be a layer as disclosed in EP 1 889 050.

Figure 3:
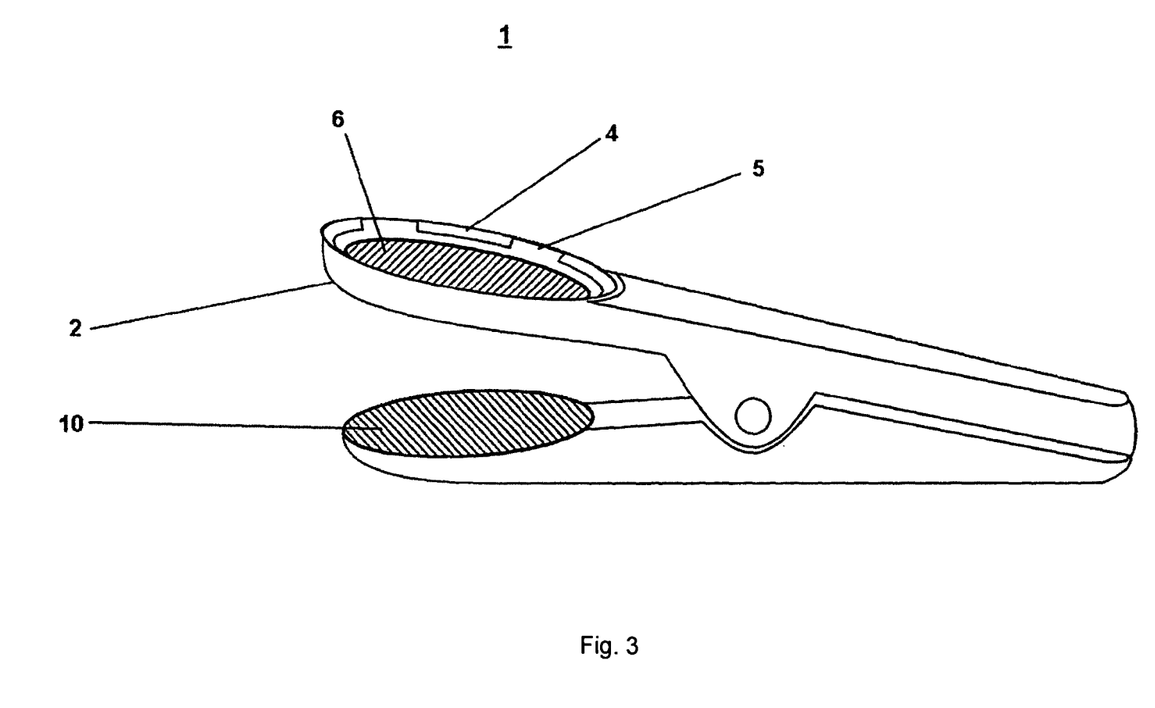
FIG. 3 a schematic view of a device for application of a sensor to a measurement site by a clamping arrangement.

FIG. 3 shows a device 1 in a clamping arrangement. A clamping arrangement is preferably clipped to an ear, ear lobe or ala of the nose. A clamping area 10 resiliently presses against the application area 2, wherein the earlobe is positioned in between the clamping area 10 and the application area 2. Additionally, the application area 2 may be covered with an adhesive layer as well as the clamping area 10. The device 1 further comprises a wall arrangement 5, which is arranged substantially perpendicular to the application area 2 in use. A membrane 6 is arranged substantially perpendicular to the wall arrangement 5 and in parallel to the application area 2 in use. The wall arrangement 5 comprises an interface 4 which enables an optical sensor head to be attached to the device 1. Optionally a contact medium layer 11 can be added to the application area. Preferably, the device 1 is made from POM (polyoxymethylene) or ABS (acrylonitrile butadiene styrene) in injection moulding.

Figure 4:
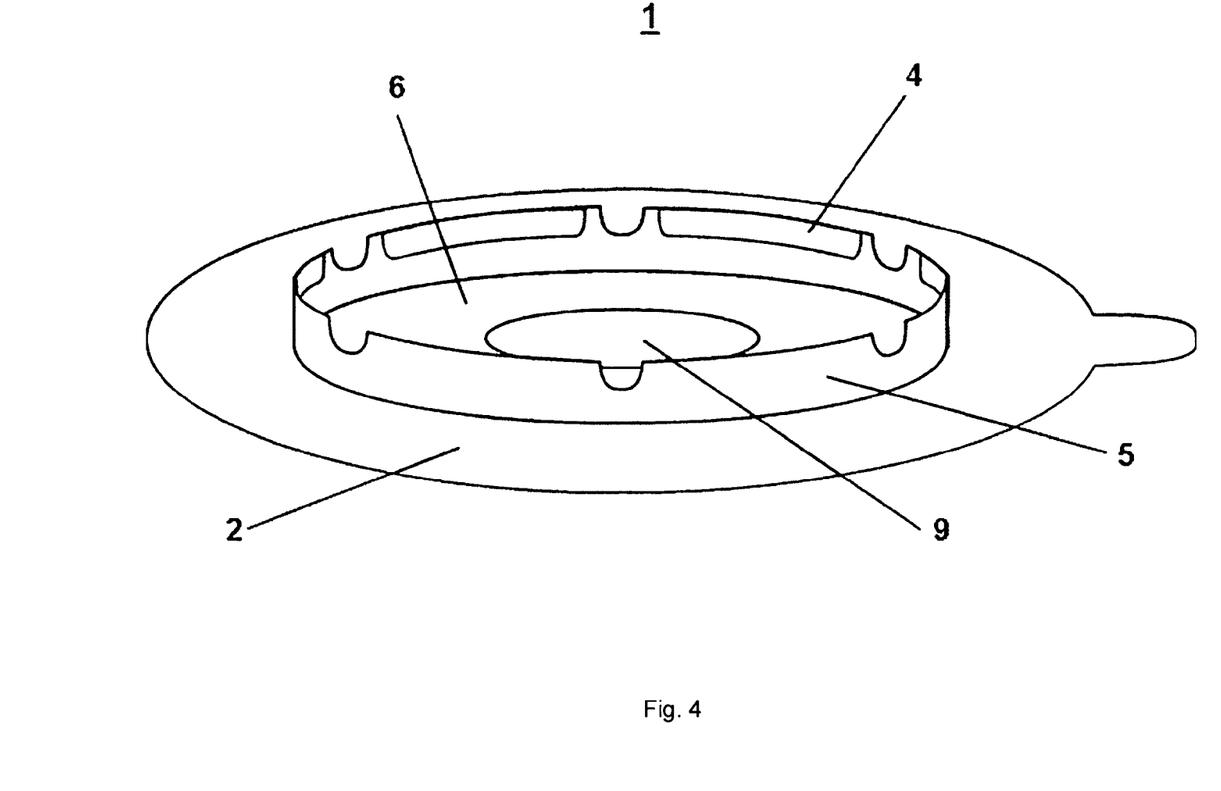
FIG. 4 a schematic view of a device for application of a sensor to a measurement site by an adhesive arrangement.

FIG. 4 shows a device 1 in an adhesive arrangement. An adhesive arrangement can basically be stuck to a measuring site anywhere. The adhesive arrangement comprises an application area 2 providing an adhesive layer. The device 1 further comprises a wall arrangement 5 which is arranged substantially perpendicular to the application area 2. A membrane 6 is provided substantially in parallel to the application area 2 in use. The wall arrangement 5 further comprises an interface 4 which enables an optical sensor head to be attached to the device 1. The device is made from plastic material and cannot be dismounted without destroying the device 1. The membrane 6 further comprises a sensitive layer 9 which does not cover the complete membrane 6. The sensitive layer 9 further comprises a reflective layer. This embodiment is preferably used for combined measurements of colorimetric and pulse oximetric measurements or measurements of spectral properties of haemoglobin and/or myoglobin and/or bilirubin and/or water and/or acetone, ethanol or other alcohols.

The invention claimed is:

1. A device for application of a sensor to a measurement site, said device comprising:
   at least one application surface enabling application of the device to a patient's skin,
   an interface for connecting the device to a sensor head,
   wherein the device has at least a wall arrangement confining an applicator volume adjacent the patient's skin, the wall arrangement comprises a patient's side and a sensor side, the device comprises at least one gas permeable membrane which separates the applicator volume into a first volume being arranged on the patient's side of the at least one gas-permeable membrane adjacent to the measurement site, and a second volume being separated from the patient's skin and adjacent to the sensor side of the at least one gas-permeable membrane, the application surface or the wall arrangement or the membrane, on the patient's side, is provided with a contact medium layer, and the contact medium is selected from the group consisting of a fluid, a gel or a paste, and wherein the gas-permeable membrane is fluid-impermeable, and the wall arrangement and the membrane are designed to be destroyed when disassembled.

2. The device according to claim 1, wherein the interface comprises a sealing element for sealing the second volume from the ambient gases and the ambient radiation during use.

3. The device according to claim 1, wherein the device further comprises at least one of an identification device and a calibration data.

4. The device according to claim 1, wherein the device contained within a gas and light-tight packaging to protect the device from both gas and light.

5. The device according to claim 1, wherein the device comprises a second fluid-impermeable membrane.

6. The device according to claim 1, wherein at least one of the contact medium layer and the application surface are covered by a detachable cover layer.

7. A device for application of a sensor to a measurement site, said device comprising:
   at least one application surface enabling application of the device to a patient's skin,
   an interface for connecting the device to a sensor head,
   wherein the device has at least a wall arrangement confining an applicator volume adjacent the patient's skin, the wall arrangement comprises a patient's side and a sensor side, the device comprises at least one gas permeable membrane which separates the applicator volume into a first volume being arranged on the patient's side of the at least one gas-permeable membrane adjacent to the measurement site, and a second volume being separated from the patient's skin and adjacent to the sensor side of the at least one gas-permeable membrane, the application surface or the wall arrangement or the membrane, on the patient's side, is provided with a contact medium layer, and the contact medium is selected from the group consisting of a fluid, a gel or a paste, and
   the second volume or the gas-permeable membrane comprises at least one gas sensitive dye.

8. The device according to claim 7, wherein a sensitive layer comprising the sensitive dye which comprises a protection layer against environmental gases and ambient light before use.

9. A device for application of a sensor to a measurement site, said device comprising:
   at least one application surface enabling application of the device to a patient's skin,
   an interface for connecting the device to a sensor head,
   wherein the device has at least a wall arrangement confining an applicator volume adjacent the patient's skin, the wall arrangement comprises a patient's side and a sensor side, the device comprises at least one gas permeable membrane which separates the applicator volume into a first volume being arranged on the patient's side of the at least one gas-permeable membrane adjacent to the measurement site, and a second volume being separated from the patient's skin and adjacent to the sensor side of the at least one gas-permeable membrane, the application surface or the wall arrangement or the membrane, on the patient's side, is provided with a contact medium layer, and the contact medium is selected from the group consisting of a fluid, a gel or a paste, and
   the gas-permeable membrane has an at least partly reflecting layer, and the at least partly reflecting layer reflects light at least in a wavelength range from 400 nm to 1 µm, or an additional at least partly reflecting layer, and the additional at least partly reflecting layer reflects light at least in a wavelength range from 400 nm to 1 µm.

10. A method for transcutaneous measurements of at least one of $CO_2$ and $O_2$ and spectral properties of haemoglobin and for pulsoximetric measurements of $O_2$ and detection of water vapour and of spectral properties of myoglobin and bilirubin and water and acetone and alcohols, the method comprising:
   providing a device comprising at least one application surface enabling application of the device to a patient's skin, an interface for connecting the device to a sensor head, wherein the device has at least a wall arrangement which confines an applicator volume adjacent the patient's skin, the wall arrangement comprises a patient's side and a sensor side, wherein the device comprises at least one gas permeable membrane which separates the applicator volume into a first volume arranged on the patient's side of the at least one gas-permeable membrane adjacent to the measurement site and a second volume separated from the patient's skin and adjacent to the sensor side of the at least one gas-permeable membrane, the application surface or the wall arrangement or the membrane, on the patient's side, is provided with a contact medium layer for engaging with the patient's skin, and the contact medium is selected from the group consisting of a fluid, a gel or a paste,
   applying the device to a measurement site,
   combining the interface of the device with an interface of a sensor head and
   carrying out at least one measurement selected from the group of:
   i.) transcutaneously measuring at least one of $CO_2$ and $O_2$,
   ii.) measuring spectral properties of haemoglobin,
   iii.) pulsoximetrically measuring $O_2$,
   iv.) detection of water vapour, and
   v.) measuring spectral properties of at least one of myoglobin, bilirubin, water, acetone and alcohol.

11. A device for application of a sensor to a measurement site, said device comprising:
   at least one application surface enabling the application of the device to a patient's skin,
   an interface for connecting the device to a sensor head,
   wherein the device has at least a wall arrangement confining an applicator volume adjacent the patient's skin, the wall arrangement comprises a patient's side and a sensor side, the device comprises at least one gas-permeable membrane which separates the applicator volume into a first volume being arranged on the patient's side of the at least one gas-permeable membrane adjacent to the measurement site and a second volume being separated from the patient's skin and adjacent to the sensor side of the at least one gas-permeable membrane, the second volume or the gas-permeable membrane comprises at least one gas sensitive dye.

12. The device according to claim 11 wherein the gas-permeable membrane is fluid-impermeable, and the wall arrangement and the membrane are designed to be destroyed when disassembled.

13. The device according to claim 11, wherein the interface comprises a sealing element for sealing the second volume from the ambient gases and the ambient radiation during use.

14. The device according to claim 11, wherein the gas-permeable membrane has an at least partly reflecting layer, and the at least partly reflecting layer-reflects light at least in a wavelength range from 400 nm to 1 µm, or an additional at least partly reflecting layer, and the additional at least partly reflecting layer reflects light at least in a wavelength range from 400 nm to 1 µm.

15. The device according to claim 11, wherein the device further comprises at least one of an identification device and a calibration data.

16. The device according to claim 11, wherein the device contained within a gas and light-tight packaging to protect the device from both gas and light.

17. The device according to claim 11, wherein a sensitive layer comprising the sensitive dye which comprises a protection layer against environmental gases and ambient light before use.

18. The device according to claim 11 wherein the device comprises a second fluid-impermeable membrane.

19. The device according to claim 11, wherein the application surface or the wall arrangement or the membrane on the patient's side is provided with a contact medium layer.

20. The device according to claim 19, wherein at least one of the contact medium layer and the application surface are covered by a detachable cover layer.

21. A method for transcutaneous measurements of at least one of $CO_2$ and $O_2$ and of spectral properties of haemoglobin and for pulsoximetric measurements of $O_2$ and detection of water vapour and of spectral properties of myoglobin and bilirubin and water and acetone and alcohols, the method comprising:

providing a device comprising at least one application surface enabling application of the device to a patient's skin, an interface for connecting the device to a sensor head, wherein the device has at least a wall arrangement which confines an applicator volume adjacent the patient's skin, the wall arrangement comprises a patient's side and a sensor side, wherein the device comprises at least one gas permeable membrane which separates the applicator into a first volume arranged on the patient's side of the at least one gas-permeable membrane adjacent to the measurement site and a second volume separated from the patient's skin and adjacent to the sensor side of the at least one gas-permeable membrane, and the second volume or the gas-permeable membrane comprises at least one gas sensitive dye, applying the device to a measurement site, combining the interface of the device with an interface of a sensor head and carrying out at least one measurement selected from the group of:
  i. transcutaneously measuring at least one of $CO_2$ and $O_2$,
  ii. measuring spectral properties of haemoglobin,
  iii. pulsoximetrically measuring Oz,
  iv. detecting water vapour, and
measuring spectral properties of at least one of myoglobin and bilirubin and water and acetone and alcohol.

* * * * *